United States Patent [19]
Hofmann et al.

[11] Patent Number: 5,209,729
[45] Date of Patent: May 11, 1993

[54] DILATATION CATHETER

[75] Inventors: Eugen Hofmann, Zurich; Susanne Pfenninger, Uster; Werner Niederhauser, Zurich, all of Switzerland

[73] Assignee: Schneider (Europe) AG, Zurich, Switzerland

[21] Appl. No.: 740,363

[22] Filed: Aug. 5, 1991

[30] Foreign Application Priority Data

Aug. 9, 1990 [CH] Switzerland .................. 2596/90

[51] Int. Cl.⁵ .................................... A61M 29/00
[52] U.S. Cl. .................................... 604/96; 606/194
[58] Field of Search .................. 604/96–97, 604/101–102, 273, 280–282; 606/192, 194

[56] References Cited

U.S. PATENT DOCUMENTS

| | | | |
|---|---|---|---|
| 4,684,363 | 8/1987 | Ari et al. | 604/98 |
| 4,877,031 | 10/1989 | Conway et al. | 604/96 X |
| 4,976,690 | 12/1990 | Solar et al. | 604/96 |
| 5,040,548 | 8/1991 | Yock | 128/898 |
| 5,046,503 | 9/1991 | Schneiderman | 128/692 |
| 5,057,073 | 10/1991 | Martin | 604/43 |
| 5,061,273 | 8/1991 | Yock | 606/194 |

Primary Examiner—C. Fred. Rosenbaum
Assistant Examiner—C. Maglione
Attorney, Agent, or Firm—Peter C. Richardson; Lawrence C. Akers; John L. LaPierre

[57] ABSTRACT

The dilatation catheter has a shaft which consists of two separately produced shaft portions. Both portions have a first lumen for a guide wire and a second lumen for a pressure liquid. The two portions overlap at a connection point and are preferably welded to one another at this point. The proximal portion consists of two coaxial tube portions and the distal portion consists of an extruded two-lumen tube piece. The proximal portion is stiffer than the distal portion, which permits an optimal adaptation to a non-straight course of a blood vessel. The dilatation catheter according to the invention is particularly suitable for the treatment of arterial occlusions, which are situated in or downstream of a vessel curve.

10 Claims, 4 Drawing Sheets

DILATATION CATHETER

BACKGROUND OF THE INVENTION

The invention relates to a dilatation catheter according to the preamble of independent Patent Claim 1. Catheters of this generic type were first developed by A. Gruntzig for percutaneous transluminal recanalization of chronic arterial occlusions and have since then been steadily increasing in importance. The catheter system used for this consists generally of a guide wire, a dilatation catheter with at least a two-lumen shaft, and a dilatation balloon arranged distally on the shaft, and also a guide catheter. The guide wire and, on it, the dilatation catheter is pushed through the guide catheter until the dilatation balloon is situated in the stricture. The balloon is now dilated with liquid, and the arteriosclerotic material is pressed radially against and into the vessel wall so that, after removal of the catheter, the vessel fluid can again pass through the treated area.

The shaft of the dilatation catheter usually consists essentially of two coaxial tube pieces, in which respect the inner tube receives the guide wire, and an intermediate space between the two tube pieces forms the lumen for the liquid for dilating the balloon. When the balloon is pushed into severe strictures, as a result of the comparatively high axial forces, the balloon and the tube connected to it are compressed, which makes the introduction of the balloon into the stricture difficult. In order to avoid this, as stiff a shaft as possible would be desirable. In contrast, if the stricture lies downstream of a vessel curve, then the shaft should be as flexible as possible in the front area, so that it can follow the vessel curve with as little friction as possible.

In order to overcome this difficulty, a two-lumen dilatation catheter has been disclosed by EP-A-0,277,368, in which the catheter the shaft is made up of several areas of different stiffness. Thus, optimum flexibility and stability should be achieved at different points along the catheter. For this purpose, shaft portions made of different materials are produced, and these are connected to one another thermoplastically.

A dilatation balloon is also known in which the two coaxial tube pieces of the shaft are connected directly behind the balloon with webs. These webs transmit the axial shear force from the outer tube to the inner tube and should prevent the abovementioned compression of the shaft during the treatment of severely stenosed vessels. Such webs make the production of the catheter considerably more difficult and expensive and they narrow the lumen for the passage of the pressure liquid.

SUMMARY OF THE INVENTION

The invention is based on the object of providing a dilatation catheter of the said generic type, which overcomes the abovementioned difficulties and which is in particular also suitable for the treatment of severely stenosed vessel portions which are situated in or downstream of a vessel bend.

The object is achieved by the invention according to claim 1.

The proximal portion of the shaft, seen in longitudinal section, has four walls, whereas the distal portion requires only three walls for the two lumina. In the case of identical or similar plastic, the proximal portion is stiffer than the distal portion.

By using plastics of differing stiffness, the difference in the stiffness of the two portions can be selected virtually as desired. The more flexible distal portion is preferably adapted in length to the length of the curved vessel portion. When the dilatation balloon is inserted into the stricture, the more flexible distal portion extends in the curved area of the vessel and the stiffer proximal portion in the substantially straight area of the vessel. In the case of a coronary stenosis, the distal portion is, for example, 15-25 cm and the proximal portion approximately 110 cm long. The longer proximal portion ensures, by means of the round cross-section of the inner tube piece, a low-friction sliding of the guide wire. The distal portion prevents a compression of the balloon, since the walls of the two lumina in this portion are not separated, and they cannot therefore be displaced in the longitudinal direction relative to each other.

According to a development of the invention, the two portions overlap at their connection points and are welded to one another at the adjacent surfaces. In this case, the portions consist of a thermoplastic, for example of a polyamide, polyurethane, polyvinylchloride, polyester, polyethylene, or another suitable plastic. Both portions can consist of the same plastic or of different plastics which can be welded to one another.

If at least one portion has reduced wall thickness at the end connected to the other portion, then it is possible to substantially avoid the shaft being harder at its said connection point than in other areas. The reduced wall thickness is advantageously achieved by means of a stretching of the end or ends in question.

BRIEF DESCRIPTION OF THE DRAWINGS

An exemplary embodiment of the dilatation catheter according to the invention will be described in greater detail below with reference to the drawings, in which:

FIG. 7 shows a longitudinal section through the front end of the dilatation catheter and through the front end of a guide wire.

DETAILED DESCRIPTION OF THE INVENTION

Figure 1:
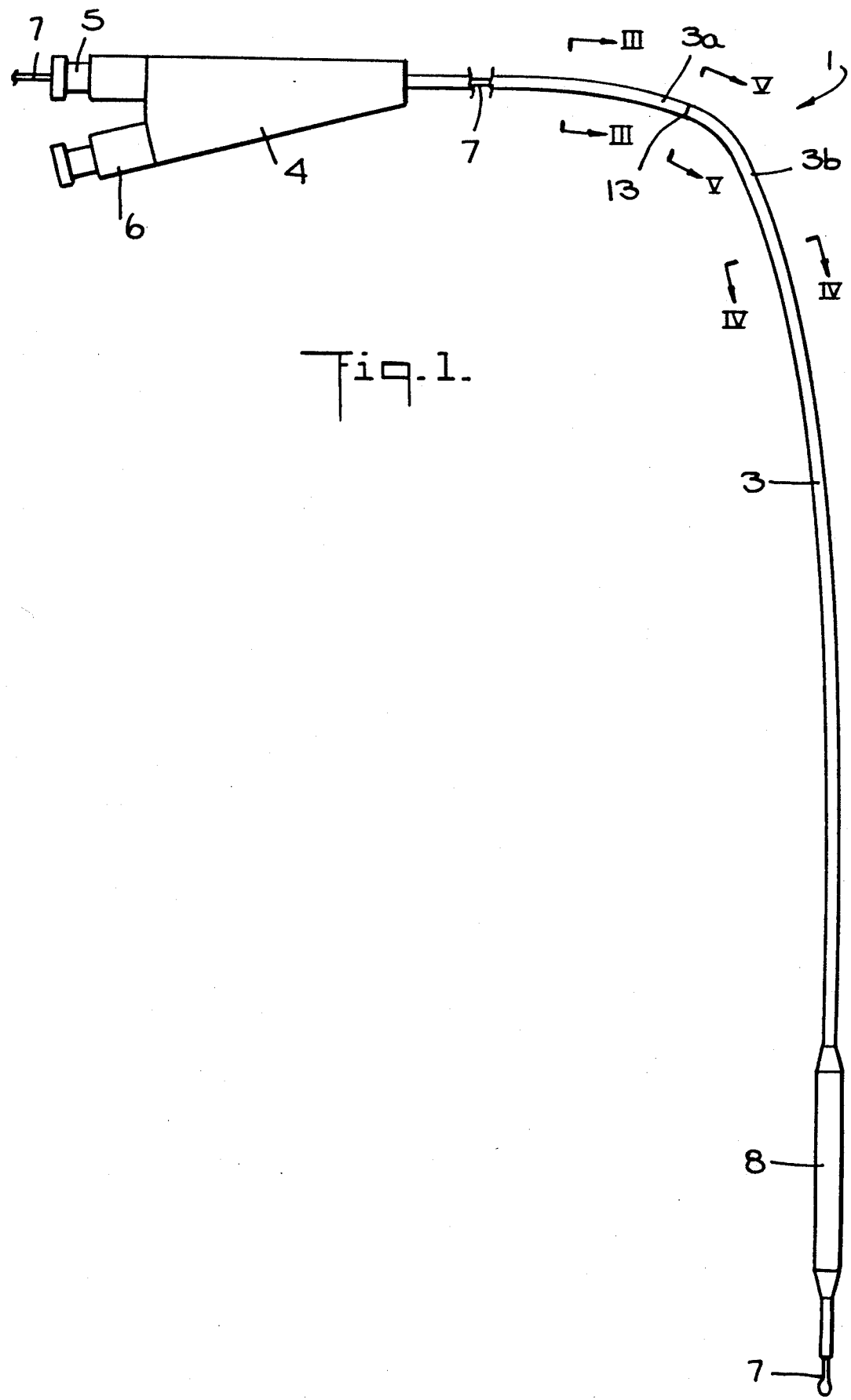
FIG. 1 shows a view of a dilatation catheter according to the invention.
Figure 6:
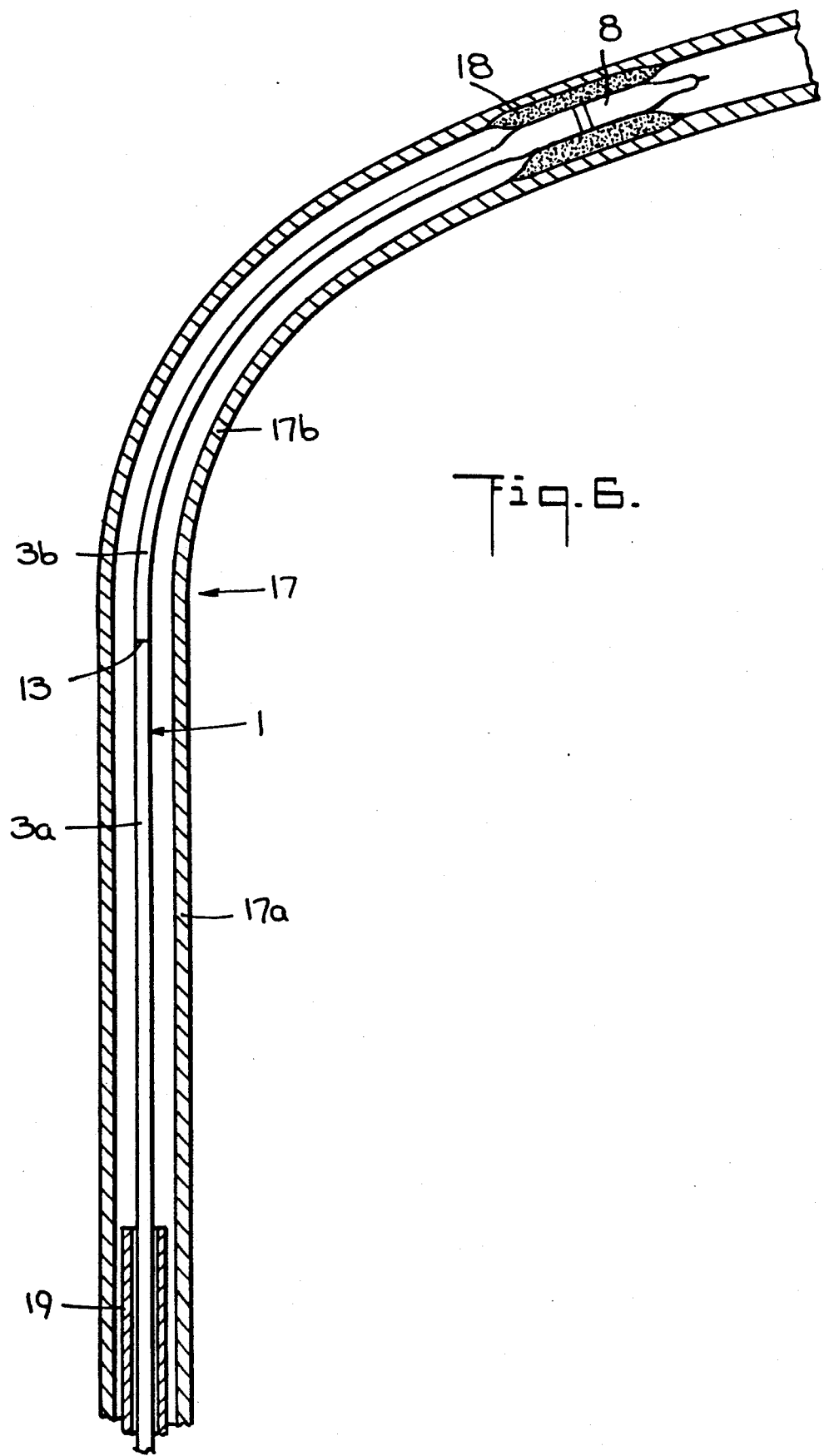
FIG. 6 shows a longitudinal section of a segment of a blood vessel with a dilatation catheter inserted.

The dilatation catheter 1 shown in FIG. 1 is inserted into a blood vessel 17 through a guide catheter 19 (FIG. 6), until the dilatation balloon 8 is situated in front of the stricture 18 to be treated. With the aid of a guide wire 7, the balloon 8, as shown in FIG. 6, is pushed into the passage through the stricture 18. The guide wire 7 is displaceable in the longitudinal direction in a continuous first lumen 11 of the dilatation catheter 1. The interior of the balloon 8 is connected via a second lumen 12 to a pressure/suction device (not shown here) which is attached to an attachment 6 of a connection piece 4. A second attachment 5 of the connection piece 4 serves for the introduction and sealing of the guide wire 7. The first lumen 11 of the dilatation catheter 1 is thus connected to the attachment 5 and the second lumen 12 to the attachment 6.

A flexible shaft 3 is connected at its distal end to the balloon 8 and at its proximal end to the connection piece 4. FIG. 7 shows the generally known balloon 8 which is connected via an opening 15 to the second lumen 12 and via this to the attachment 6. By means of the said pressure/suction device, the balloon 8 can be folded for its introduction into the vessel 17 and dilatated for treatment of the stenosis 18. As shown in FIG. 7, the distal end of the guide wire 7 can be pushed past the dilatation balloon 8 through an opening 16. As is known, it is particularly flexible and yet torsion-proof at its distal end.

Figure 4:
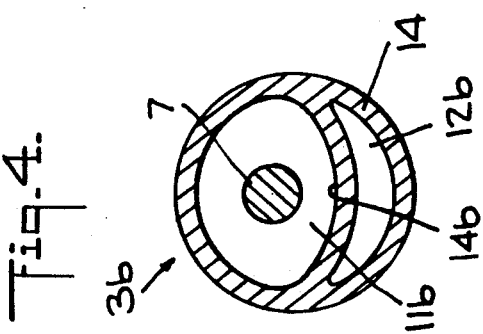
FIG. 4 shows a cross-section along the line IV—IV in FIG. 1.
Figure 3:
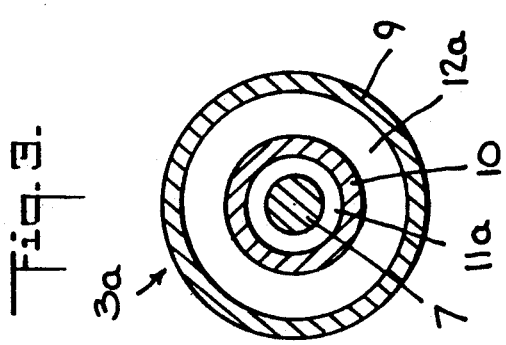
FIG. 3 shows a cross-section along the line III—III in FIG. 1.

The shaft 3 is made of up a proximal portion 3a and a distal portion 3b. These portions 3a and 3b are produced separately and are connected to one another at the connection point 13. As FIGS. 3 and 4 show, the cross-sections of the two portions 3a and 3b are different. The proximal portion 3a consists of two coaxial tube pieces 9 and 10, in which respect the inner tube piece 10 forms a lumen 11a for the guide wire 7. The intermediate space between the tube pieces 9 and 10 forms a lumen 12a in which pressure liquid circulates between the balloon 8 and the pressure/suction pump. The tube pieces 9 and 10 have a circular cross-section and consist of a thermoplastic. The shaft portion 3a is connected firmly to the connection piece 4 in a known manner.

The shaft portion 3b consists of a two-lumen, extruded tube piece 14, which is connected to the balloon 8 in a known manner. A first approximately circular lumen 11b serves for receiving the guide wire 7, and a second crescent-shaped lumen 12b serves for receiving the pressure liquid. Both lumina are separated from one another by a separating wall 13b formed on portion 3b.

Figure 2:
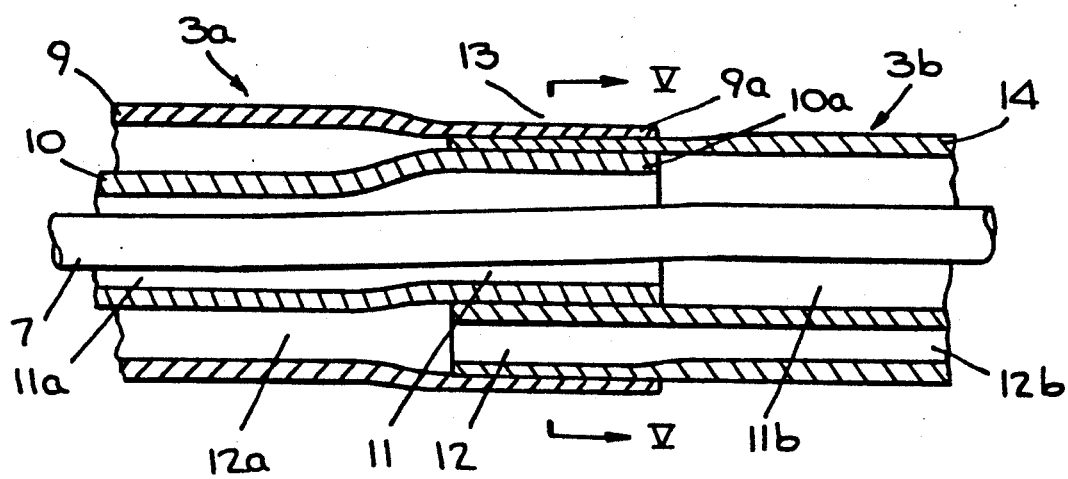
FIG. 2 shows a longitudinal section through a portion of the shaft.
Figure 2A:
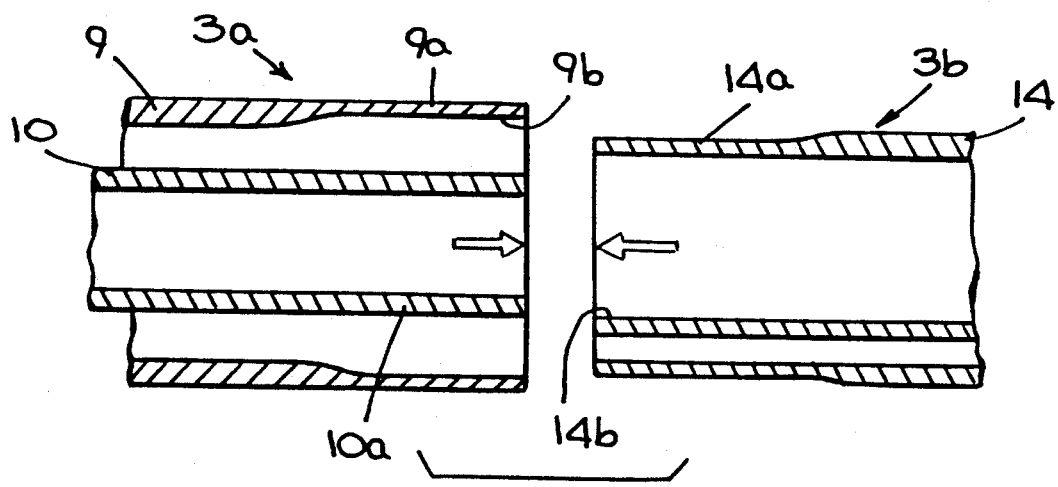
FIG. 2a shows the ends of two shaft portions in longitudinal section and before these portions are joined together.
Figure 2:
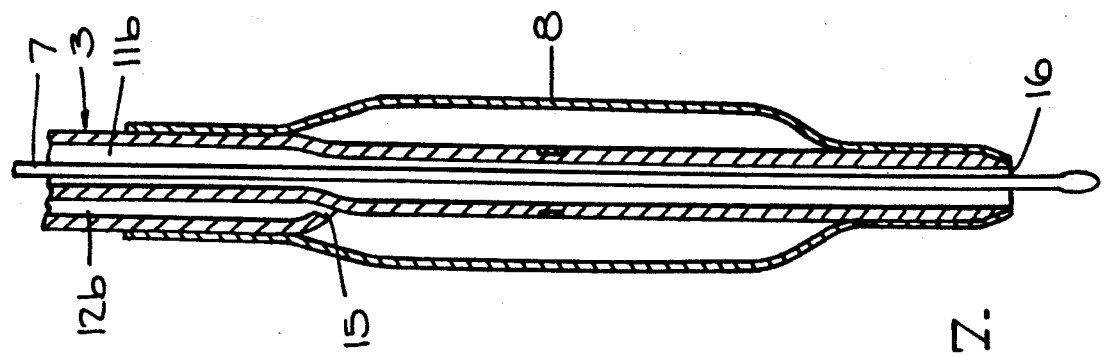
Figure 5:
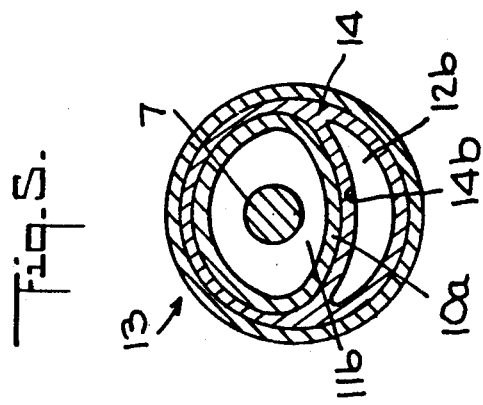
FIG. 5 shows a cross-section along the line V—V in FIGS. 1 and 2.

According to FIG. 2, the portions 3a and 3b are connected to one another in such a way that the lumina 11a and 11b form the first lumen 11 and the lumina 12a and 12b form the lumen 12. The lumina 11 and 12 are thus completely separate from one another even at the connection point 13. In order to connect the separately produced portions 3a and 3b to one another, these portions are pushed together until the corresponding ends overlap by a length of a few millimeters. As FIG. 2a shows, the tube piece 9 is preferably stretched in the longitudinal direction at the end to be connected and has an area 9a of reduced wall thickness. This prevents the outer diameter of the shaft 3 at the connection point 13 from being substantially greater than outside this area.

In the area of the connection point 13, the two tube portions 3a and 3b are preferably welded to one another. The outer surface 14a of the tube piece 14 is preferably welded to the inner surface 9b of the tube piece 9, and the outer side 10a of the tube piece 10 is preferably welded to the inner side 14b of the tube piece 14. A design is also possible in which the tube piece 14 has a reduced wall thickness at the end to be connected. This reduced wall thickness can also be obtained here, for example, by abrading the tube piece 14 on the outer side 14a. A design is also conceivable in which the two portions 3a and 3b are glued to one another at the overlapping area 13.

If the portions 3a and 3b are made of identical or similar plastic and if the wall thicknesses are approximately the same, then the tube piece 3a has greater stiffness than the tube piece 3b. The main reason for the different stiffness is that the tube piece 3a in the longitudinal section according to FIG. 2 consists of four wall areas and the portion 3b consists only of three wall areas. The differing stiffness thus arises primarily from the different structures of the two portions 3a and 3b.

The length of the more flexible portion 3b is preferably adapted to the length of the curved portion of the blood vessel 17 to be treated, as is shown diagrammatically in FIG. 6. The vessel stricture 18 is here situated, seen in the direction of flow of the vessel fluid, in or downstream of a vessel curve 17b, and the latter in turn leads on to a substantially straight vessel portion 17a. Upon introduction of the dilatation catheter 1 into the vessel, and in particular upon introduction of the balloon 8 into the stricture 18, the more flexible portion 3b can easily follow the curve of the vessel 17 with little risk of injury. Since the portion 3b has the cross-section shown in FIG. 4, a compression of the balloon 8 in the longitudinal direction is not to be expected even if the stricture 18 offers comparatively great resistance to a displacement of the catheter. The guide wire 7 slides particularly easily in the stiff but substantially straight portion 3a, since the lumen 11a is substantially circular. This can be further improved by appropriate coating of the guide wire 7 and the inner side of the tube piece 10. The vessel course shown in FIG. 6 is typical in many treatment cases. A design is also conceivable in which both portions 3a and 3b or one of these portions have/has more than two lumina. Thus, for example, the portion 3b can have four lumina.

We claim:

1. A dilation catheter for percutaneous transluminal recanalization of chronic arterial occlusions comprising a shaft having proximal and distal ends and a first shaft lumen extending therebetween, a dilatation balloon located proximate said distal end, with said first shaft lumen being adapted to receive a guide wire and with said shaft having a second shaft lumen for pressurizing said balloon, said shaft comprising at least two separately produced segments connected to one another wherein said segments include a proximal portion having two coaxial tube pieces defining inner and outer lumens and a more flexible distal portion having a two-lumen tube piece, said portions being connected to one another such that a first lumen of the distal portion is connected to said inner lumen of the proximal portion, and a second lumen of the distal portion is connected to said outer lumen of the proximal portion.

2. The dilatation catheter according to claim 1 wherein the two portions overlap at their connection point and are welded to one another along adjacent surfaces.

3. The dilatation catheter according to claim 2 wherein at least one portion has a reduced wall thickness at the end connected to the other portion.

4. The dilatation catheter according to claim 3 wherein the end of the distal portion connected to the proximal portion is stretched in the longitudinal direction.

5. The dilatation catheter according to claim 3 wherein, at the connection point, the inner tube piece of the proximal portion is inserted into a first lumen of the distal portion and said outer lumen of the proximal portion is connected to a second lumen of the distal portion.

6. The dilatation catheter according to claim 2 wherein, at the connection point, the inner tube piece of the proximal portion is inserted into a first lumen of the distal portion and said outer lumen of the proximal portion is connected to a second lumen of the distal portion.

7. The dilatation catheter according to claim 1 wherein at least one portion has a reduced wall thickness at the end connected to the other portion.

8. The dilatation catheter according to claim 7 wherein the end of the distal portion connected to the proximal portion is stretched in the longitudinal direction.

9. The dilatation catheter according to claim 7 wherein, at the connection point, the inner tube piece of the proximal portion is inserted into a first lumen of the distal portion and said outer lumen of the proximal portion is connected to a second lumen of the distal portion.

10. The dilatation catheter according to claim 1 wherein the two portions are glued to one another.

* * * * *